United States Patent [19]
Springmann

[11] Patent Number: 6,022,510
[45] Date of Patent: Feb. 8, 2000

[54] GAS-SAMPLING MEANS FOR A FLUE-GAS ANALYSIS APPARATUS

[75] Inventor: Thomas Springmann, Freiburg, Germany

[73] Assignee: Testoterm Fritzsching GmbH & Co., Lenzkirch, Germany

[21] Appl. No.: 08/060,922

[22] Filed: May 13, 1993

[30] Foreign Application Priority Data

May 18, 1992 [DE] Germany .............................. 42 16 404

[51] Int. Cl.[7] ............................................ B01L 3/12
[52] U.S. Cl. ..................... 422/101; 422/78; 73/863.12; 73/863.23; 73/863.24; 73/863.25; 73/864.73
[58] Field of Search ................... 422/101.78; 55/302; 73/863.12, 863.23, 863.24, 863.25, 864.73; 423/243.08

[56] References Cited

U.S. PATENT DOCUMENTS

| | | | |
|---|---|---|---|
| 3,006,194 | 10/1961 | Greene et al. | 73/863.12 |
| 3,758,668 | 9/1973 | Lapple et al. | 423/242 |
| 3,759,087 | 9/1973 | Iwao et al. | 73/23 |
| 3,881,359 | 5/1975 | Culbertson | 73/421.57 |
| 4,133,657 | 1/1979 | Krogsrud | 55/290 |
| 4,247,313 | 1/1981 | Perry et al. | 55/302 |
| 4,344,917 | 8/1982 | Schorno | 422/78 |
| 4,379,412 | 4/1983 | Wood | 73/863.24 |
| 4,681,609 | 7/1987 | Howeth | 55/302 |
| 4,772,454 | 9/1988 | Jarolics | 422/101 |
| 4,821,585 | 4/1989 | Kempe | 73/863.23 |
| 4,973,458 | 11/1990 | Newby et al. | 423/244 |
| 4,974,455 | 12/1990 | McGowan et al. | 73/863.12 |
| 4,984,476 | 1/1991 | Dahrendorf et al. | 73/864.35 |
| 5,000,051 | 3/1991 | Bredemeier | 73/863.23 |
| 5,039,322 | 8/1991 | Hözl | 55/302 |

FOREIGN PATENT DOCUMENTS

| | | |
|---|---|---|
| 0324330 | 11/1988 | European Pat. Off. . |
| 1949081 | 9/1969 | Germany . |
| 2416576 | 5/1974 | Germany . |

OTHER PUBLICATIONS

Patent Abstracts of Japan, vol. 005069, Group P060, May 1981.

*Primary Examiner*—Jill Warden
*Attorney, Agent, or Firm*—Thelen Reid & Priest

[57] ABSTRACT

A gas-sampling tube for a flue-gas analysis apparatus having therein a particle filter and a measured gas line downstream of it. A heating jacket comprising an electric heater is located in the gas-sampling tube and extends axially co-extensive with the measured gas line and the particle filter, and in surrounding relation to them.

3 Claims, 1 Drawing Sheet

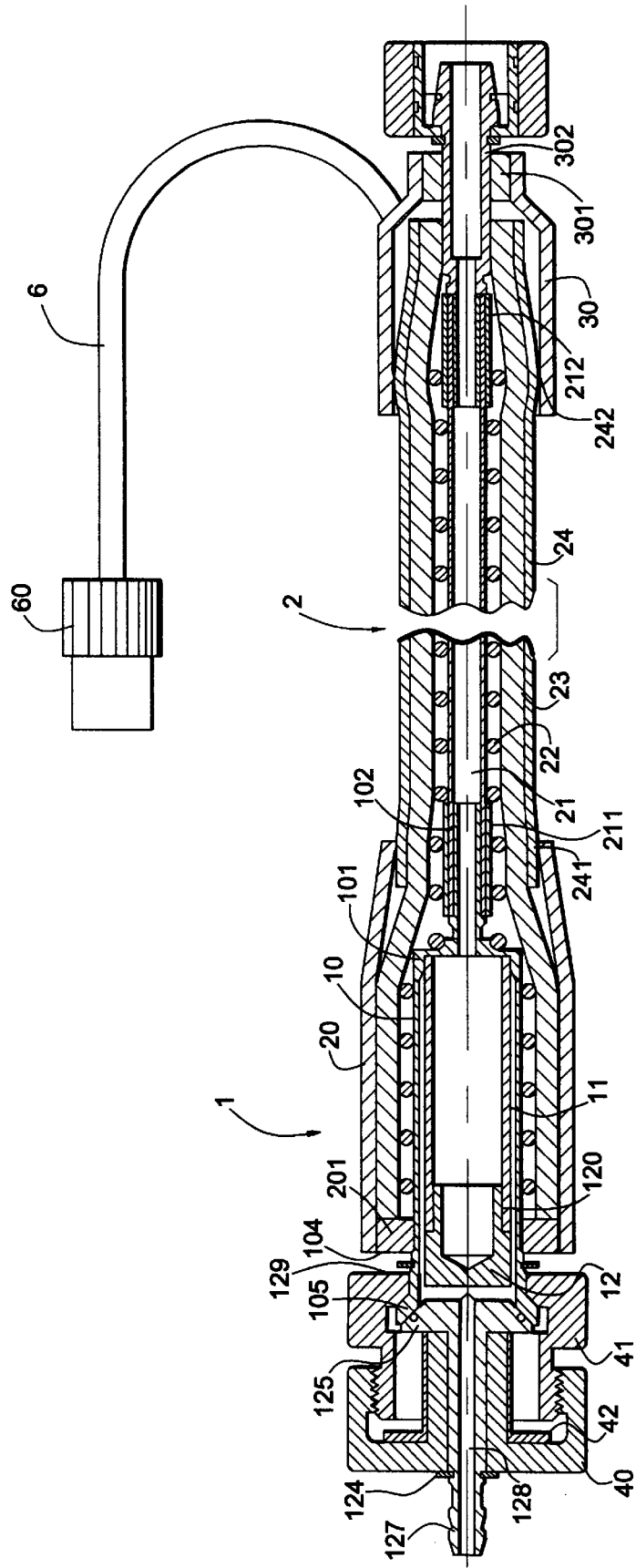

GAS-SAMPLING MEANS FOR A FLUE-GAS ANALYSIS APPARATUS

The invention relates to a gas-sampling means for a flue-gas analysis apparatus.

BACKGROUND OF THE INVENTION

For analysis of the flue gas of furnace installations, the flue gas is sucked in by means of a probe and fed to an analysis apparatus. The flue gas must be treated prior to analysis thereof, i.e., it is necessary in particular to remove smoke and dirt particles as well as moisture from the flue gas.

The flue gas is passed from the probe through a tube to the analysis apparatus. If condensate is deposited in the tube, the flue gas in the tube comes into contact with the liquid condensate over a long period of time. In the process, $NO_2$ and $SO_2$ are partly fixed in the liquid condensate, resulting in measurement errors.

It is known that such measurement errors can be prevented by using a heated tube. In the tube, the flue gas is heated to a temperature above the dew point, with the result that condensate is not deposited. The entire deposition of condensate takes place in a cooled condensate trap incorporated upstream from the analysis apparatus. Thereby, the condensate is collected rapidly and within a short section of the gas-flow path, and so the duration of contact of the gas with the liquid condensate is limited and $NO_2$ and $SO_2$ are fixed to only a slight extent, with a nonsignificant falsifying influence on the measured result.

It is known that a filter can be interposed between the flue-gas probe and the heatable tube for the purpose of removing dirt and soot particles from the flue gas being fed to the analysis apparatus. A disadvantage of this expedient is that condensate can be deposited in this filter. This leads to the aforesaid falsification of the measured result, since $NO_2$ and $SO_2$ become partly fixed in the condensate. In addition, the moisture of the condensate in the filter leads to more rapid fouling of the filter by dirt and smoke particles.

To circumvent this problem, it has been suggested in West German Laid-open Application 1,949,081 that the filter be equipped with an electrical heating device. This is located inside a housing, and is constructed, for example, in the form of a helical heating coil around the filter element, which is also located in the housing. This makes it possible to keep the temperature of the flue gas above the dew point. The disadvantage of such a configuration lies in the fact that the heatable tube and the upstream heatable filter are provided as separate units, each with its own heating system. The necessary expense is high; problems occur in particular with respect to dimensions and weight, if the analysis of the flue gas is to be undertaken not by fixed units but instead by mobile units.

The object of the invention was therefore to provide, for a flue-gas analysis apparatus, a gas-sampling means that does not have the described disadvantages. As regards the possibility of mobile use, a particular object is to provide a gas-sampling means of light weight and small dimension.

SUMMARY OF THE INVENTION

The present invention provides a structure in which the particle filter is integrated in the gas-sampling tube. At the same time, the need for a separate heating system specific to the particle filter is obviated, because the particle filter is heated in a temperature-controlled manner by the heating jacket of the measured-gas line. Structural complexity is greatly reduced by this construction, since no only is the otherwise separate heating system for the particle filter completely eliminated, but also no additional connections for the electricity supply are necessary. Operation is also greatly simplified, since separate handling of the particle filter is not needed and thus operator's errors are proportionally precluded.

BRIEF DESCRIPTION OF THE DRAWING

The invention will be explained in more detail in the following by reference to the FIGURE, which schematically shows the measured-gas means according to the invention in sectional representation.

DESCRIPTION OF THE PREFERRED EMBODIMENT

The measured-gas means consists substantially of the particle filter 1 and the gas-sampling tube 2.

The gas-sampling tube 2 has a measured-gas line 21, which is surrounded by a heating coil 22. The heating coil 22 is completely surrounded by an insulating layer 23 in the manner of a tubular sheath. The heating coil 22 and the insulating layer 23 form the so-called heating jacket. The heating coil 22 is supplied with electrical energy through a lead line 6, which is connected via a coupling 60 in a manner not shown in more detail here with the electricity source, which is also not shown here. For protection against mechanical damage, reinforcement 24 is provided that completely encloses the heating jacket in the manner of a tubular sheath.

The particle filter 1 contains a filter element 11. This has the form of a hollow cylinder, through which the flue gas flows in radial direction from outside to inside. During passage of the flue gas through the filter element 11, the dirt and dust particles are held back, while the flue gas freed of dust and dirt particles enters the measured-gas line 21 and flows therethrough. The particle filter is integrated coaxially in the gas-sampling tube 2, in the inlet end thereof. For this purpose, the heating jacket is extended coaxially beyond the end of the measured-gas line 21 to enclose the particle filter. In its axial extension it is guided almost completely around the particle filter 1, and so the flue gas is already influenced by the heating action as soon as it has entered the region of the particle filter 1, undesired cooling of the flue gas thereby being avoided.

The cylindrical filter element 11 is mounted centrally in a coaxial filter housing 10. The filter housing 10 also has cylindrical form. Its outside wall is in contact with the heating coil 22. The inside diameter of the filter housing 10 is selected to ensure that an admission zone for the entering flue gas will be formed between the inside wall of the filter housing 10 and the filter element 11 mounted centrally therein.

For centering the filter element 11, a closure plug 12 for the filter housing 10 is provided at the admission end. The closure plug 12 projects with a centering neck 120 into the inside of the filter housing 10. The centering neck 120 engages in the inside of the cylindrical filter element 11. At the discharge end, the filter element 11 is centered by a shouldered web 101, which is located on the inside of the filter housing 10.

The closure plug 12 has a cone 125, which is brought into contact with the funnel-shaped seal 105 of the filter housing 10. Fixing in position is achieved by means of threaded elements 40, 41, which permit simple replacement of the filter element 11. A union nut 40 engages with a clamping sleeve 41, which is braced against the back side of the funnel-shaped seal 105 on the filter housing 10. The union nut acts on a spacer sleeve 42, which in the rear region of the cone 125 presses on the closure plug 12. By tightening the union nut 40, the closure plug 12, by means of the cone 125, is therefore clamped together with the filter housing 10, at the funnel-shaped seal 105 on the filter housing. One locking ring 104 each is mounted on the filter housing 10 and on the closure plug 12, in order to limit the axial displacement of the threaded elements 40, 41 in the opened condition.

At its front end the closure plug 12 also has a connecting nipple 127, to which a gas-sampling probe can be attached in a manner not shown here. Feeding of the flue gas to the filter element 11 is achieved via guide ducts 128, 129, which are provided in the form of holes in the closure plug 12. Thus, the flue gas enters the guide duct 128 axially and is passed through the radially directed guide duct 129 into the intermediate space between the filter housing 10 and the filter element 11.

To increase the mechanical stability, the gas-sampling tube 2 has cover sleeves 20, 30 on both the inlet and outlet sides. At the inlet end, the cover sleeve 20 extends axially in the region of the particle filter 1. The cover sleeve 20 is closed at the end by a bearing ring 201, which holds the filter housing 10. At its other end, the cover sleeve 20 is guided over the reinforcement 24, which in the overlapping region has a low prominence in the form of a bead 241. Thereby a clamping action is achieved between the cover sleeve 20 and the reinforcement 24, which action functions on the one hand as a sealing device and on the other as a strain-relief device.

At the exit end, the clamping sleeve 30, through which the electrical lead line 6 for the heating coil 22 is guided, is attached in the same way. The cover sleeve 30 also has a bearing ring 301, which holds an exit-end connecting nipple 302.

At the exit end the gas-sampling tube 2 also has a bead 242, which is surrounded clampingly by the cover sleeve 30.

The beads 241 and 242 are formed by the fact that clamping sleeves 211 and 212 are pushed over the measured-gas line 21 in the region of the transition nipple 102 or of the connecting nipple 302, with the result that the heating jacket, including the reinforcement 24, is displaced radially outward at these positions.

The claims and specification describe the invention presented, and the terms that are employed in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

I claim:

1. A gas sampling tube for flue-gas analysis comprising:

a gas inlet constructed and adapted to receive a flue-gas sample;

an elongate filter element downstream of said gas inlet and in fluid communication with said gas inlet for normally receiving gas from said gas inlet;

a measured gas line downstream of said filter element and in fluid communication with said filter element for normally receiving gas from said filter element;

a gas outlet downstream of said measured gas line;

a single heater extending substantially the length of said filter element and said measured gas line for heating said filter element and said measured gas line;

a cylindrical housing, said filter element being within said housing and being in the form of a hollow cylinder; and a closure plug at the inlet of said filter housing, said closure plug having ducts therein for directing gas outwardly, said filter element having an external diameter less than the internal diameter of said filter housing, to provide a space therebetween for receiving gas passing through said ducts, and said closure plug having a centering neck entered into and supporting said filter element.

2. The gas-sampling tube according to claim 1, and further comprising means for detachably holding said closure plug to said cylindrical housing.

3. A gas sampling tube for flue-gas analysis comprising:

a gas inlet constructed and adapted to receive a flue-gas sample;

an elongate filter element downstream of said gas inlet and in fluid communication with said gas inlet for normally receiving gas from said gas inlet;

a measured gas line downstream of said filter element and in fluid communication with said filter element for normally receiving gas from said filter element;

a gas outlet downstream of said measured gas line;

a single heater extending substantially the length of said filter element and said measured gas line for heating said filter element and said measured gas line; and an insulating layer in surrounding relationship to said heater, said heater and said insulating layer being of tubular configuration.

* * * * *